US00PP12036P2

(12) United States Plant Patent
Cascante

(10) Patent No.: US PP12,036 P2
(45) Date of Patent: Aug. 7, 2001

(54) DOUBLE IMPATIENS PLANT NAMED 'CAMEO SCARLET'

(75) Inventor: Xenia Cascante, Alajuela (CR)

(73) Assignee: Oglevee Ltd., Connellsville, PA (US)

( * ) Notice: Subject to any disclaimer, the term of this patent is extended or adjusted under 35 U.S.C. 154(b) by 0 days.

(21) Appl. No.: 09/512,632

(22) Filed: Feb. 25, 2000

(51) Int. Cl.[7] ..... A01H 5/00
(52) U.S. Cl. ..... Plt./319

(58) Field of Search ..... Plt./317, 319

*Primary Examiner*—Bruce R. Campell
*Assistant Examiner*—Michelle Kizilkaya
(74) *Attorney, Agent, or Firm*—C. A. Whealy

(57) ABSTRACT

A new and distinct cultivar of Double Impatiens plant named 'Cameo Scarlet', characterized by its extremely large scarlet-colored flowers; fully double flower form; freely flowering habit with flowers positioned above the foliage; compact, mounded, somewhat spreading, densely foliated, and freely branching plant habit; and large rounded dark green leaves.

1 Drawing Sheet

BACKGROUND OF THE INVENTION

The present Invention relates to a new and distinct cultivar of Double Impatiens plant, botanically known as *Impatiens walleriana*, and hereinafter referred to by the cultivar name 'Cameo Scarlet'.

The new Impatiens is a product of a planned breeding program conducted by the Inventor in Cartago, Costa Rica. The objective of the breeding program was to develop new compact Double Impatiens cultivars with large fully double flowers, excellent branching, and interesting flower and foliage colors.

The new Impatiens originated from a cross made by the Inventor of the *Impatiens walleriana* cultivar Confection Orange, not patented, as the male, or pollen parent, with the *Impatiens walleriana* cultivar Impulse Scarlet, not patented, as the female, or seed parent. The cultivar Cameo Scarlet was discovered and selected by the Inventor as a flowering plant within the progeny of the stated cross in a controlled environment in Cartago, Costa Rica.

Plants of the new Impatiens differ from plants of the male parent, the cultivar Confection Orange, in the following characteristics:

1. Plants of the new Impatiens have fully double scarlet flowers whereas plants of the cultivar Confection Orange have semi-double orange flowers.

2. Flowers of plants of the new Impatiens are sterile whereas flowers of plants of the cultivar Confection Orange are fertile.

3. Plants of the new Impatiens are shorter than plants of the cultivar Confection Orange.

Plants of the female parent, Impulse Scarlet, and plants of the new Impatiens differ in the following characteristics:

1. Plants of the new Impatiens have fully double scarlet flowers whereas plants of the cultivar Impulse Scarlet have single dar k scarlet flowers.

2. Flowers of plants of the new Impatiens are sterile whereas flowers of plants of the cultivar Impulse Scarlet are fertile.

3. Plants of the new Impatiens are shorter than plants of the cultivar Impulse Scarlet.

Asexual reproduction of the new cultivar by terminal cuttings taken at Cartago, Costa Rica, has shown that the unique features of this new Impatiens are stable and reproduced true to type in successive generations of asexual reproduction.

SUMMARY OF THE INVENTION

The following traits have been repeatedly observed and are determined to be the unique characteristics of 'Cameo Scarlet'. These characteristics in combination distinguish 'Cameo Scarlet' as a new and distinct cultivar:

1. Extremely large scarlet-colored flowers; freely flowering.

2. Fully double flower form.

3. Freely flowering habit.

4. Flowers positioned above the foliage.

5. Compact, mounded and somewhat spreading plant habit.

6. Freely branching habit.

7. Large rounded dark green leaves; densely foliated.

The new Impatiens can be compared to the *Impatiens walleriana* cultivar Salsa Red U.S. Plant Pat. No. 9,606. However, in side-by-side comparisons conducted in Lompoc, Calif., plants of the new Impatiens differ from plants of the cultivar Fiesta Salsa Red in the following characteristics:

1. Plants of the new Impatiens and plants of the cultivar Fiesta Salsa Red differ in flower color, 44B and 46B, respectively.

2. Flowers of plants of the new Impatiens are about 25% larger and have more petals than flowers of plants of the cultivar Fiesta Salsa Red.

3. Leaves of plants of the new Impatiens are more rounded than leaves of plants of the cultivar Fiesta Salsa Red.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which more accurately describe the actual colors of the new Impatiens. The photograph comprises a close-up view of typical flowers and leaves of 'Cameo Scarlet'.

DETAILED BOTANICAL DESCRIPTION

The cultivar Cameo Scarlet has not been observed under all possible environmental conditions. The phenotype may vary somewhat with variations in environment such as temperature and light intensity, without, however, any variance in genotype. The photographic illustrations and the following observations, measurements and comparisons describe about 6 week old plants grown in 10 cm pots in Lompoc, Calif., under commercial practice in a fiberglass-covered greenhouse with day temperatures about 21 to 24° C., night temperatures about 16 to 18° C. and light levels generally about 3,000 to 4,000 footcandles.

In the following description, color references are made to The Royal Horticultural Society Colour Chart except where general terms of ordinary dictionary significance are used.

Botanical classification: *Impatiens walleriana* cultivar Cameo Scarlet.

Parentage:

*Male parent.*—*Impatiens walleriana* cultivar Confection Orange, not patented.

*Female parent.*—*Impatiens walleriana* cultivar Impulse Scarlet, not patented.

Propagation:

*Type cutting.*—Terminal cuttings.

*Time to initiate roots.*—Summer: About 10 days with 21° C. Winter: About 12 days at 21° C.

*Time to produce a rooted cutting or liner.*—Summer and winter: About 28 days at 21° C.

*Rooting habit.*—Numerous, fibrous, fine and freely branching.

Plant description:

*General appearance.*—Compact, mounded and somewhat spreading. Appropriate for 10 to 15-cm pots to 20 and 25-cm hanging basket containers.

*Growth and branching habit.*—Freely-branching with at least ten lateral branches at the base, dense and bushy growth. Pinching, that is, removal of the terminal apices, is typically not required. Vigorous and rapid growth rate.

*Crop time.*—10-cm pot: Without pinching, about 5 to 6 weeks. 25-cm hanging basket container: Without pinching, about 8 to 10 weeks; with a soft pinch, about 6 to 8 weeks.

*Plant height.*—About 18 cm.

*Plant spread.*—24 cm.

*Lateral branches.*—Length: About 18 to 20 cm. Diameter: About 6 to 10 mm. Internode length: About 1 to 2.5 cm. Color: Light green with some purplish anthocyanin coloration on older stems.

*Foliage description.*—Leaves simple, alternate; broad and rounded, generally symmetrical; abundant, densely foliated. Length: About 4 cm. Width: About 3 cm. Shape: Ovate. Apex: Acute. Base: Acute. Margin: Slightly serrate. Texture: Glabrous. Color: Young foliage, upper surface: 137A. Young foliage, lower surface: 148C. Fully expanded foliage, upper surface: 147A. Fully expanded foliage, lower surface: 147B. Venation, upper surface: 147B. Venation, lower surface: 138A. Petiole: Length: About 1 to 2 cm. Diameter: About 2 to 3 mm. Color: 147B.

Flower description:

*Flower type and habit.*—Numerous and consistently double scarlet-colored flowers. Freely and continuously flowering. Flower buds open similar to a rose in fullness. Flowers arise from leaf axils. Usually about 8 to 15 flowers and flower buds per lateral branch and about 75 to 100 flowers and flower buds on a mature plant. Flowers positioned above the foliage and typically face outward to upward. Flowers generally flat and rounded. Flowers last about 7 to 10 days on the plant depending on temperature and weather conditions. Flowers not persistent. Flowers not fragrant.

*Flowering season.*—Year-round under greenhouse conditions. In the garden, flowering is continuous from spring until fall.

*Flower size.*—Diameter: About 5 cm. Depth: About 2 cm.

*Flower buds.*—Rate of opening: From showing color to fully open flower, about 5 to 7 days is typical depending on temperature. Length: About 1.6 cm. Diameter: About 1.2 cm. Shape: Obovate.

*Petals.*—Quantity/arrangement: About 30 to 35 per flower; imbricate. Length: About 2.2 cm. Width: About 1.8 cm. Shape: Ovate to cordate. Apex: Rounded to indented. Base: Rounded to acute. Margin: Entire. Texture: Smooth. Color: When opening, upper surface: 43A. When opening, lower surface: 41A. Fully opened, upper surface: 44B, fading to 44C. Fully opened, lower surface: 41B.

*Peduncles.*—Length: About 2.5 cm. Angle: About 45° to the lateral branch. Strength: Strong.

*Reproductive organs.*—None observed.

Disease resistance: Plants of the new Impatiens have demonstrated good resistance to pathogens common to Impatiens.

Seed development: Seed production has not been observed.

It is claimed:

1. A new and distinct cultivar of Double Impatiens plant named 'Cameo Scarlet', as illustrated and described.

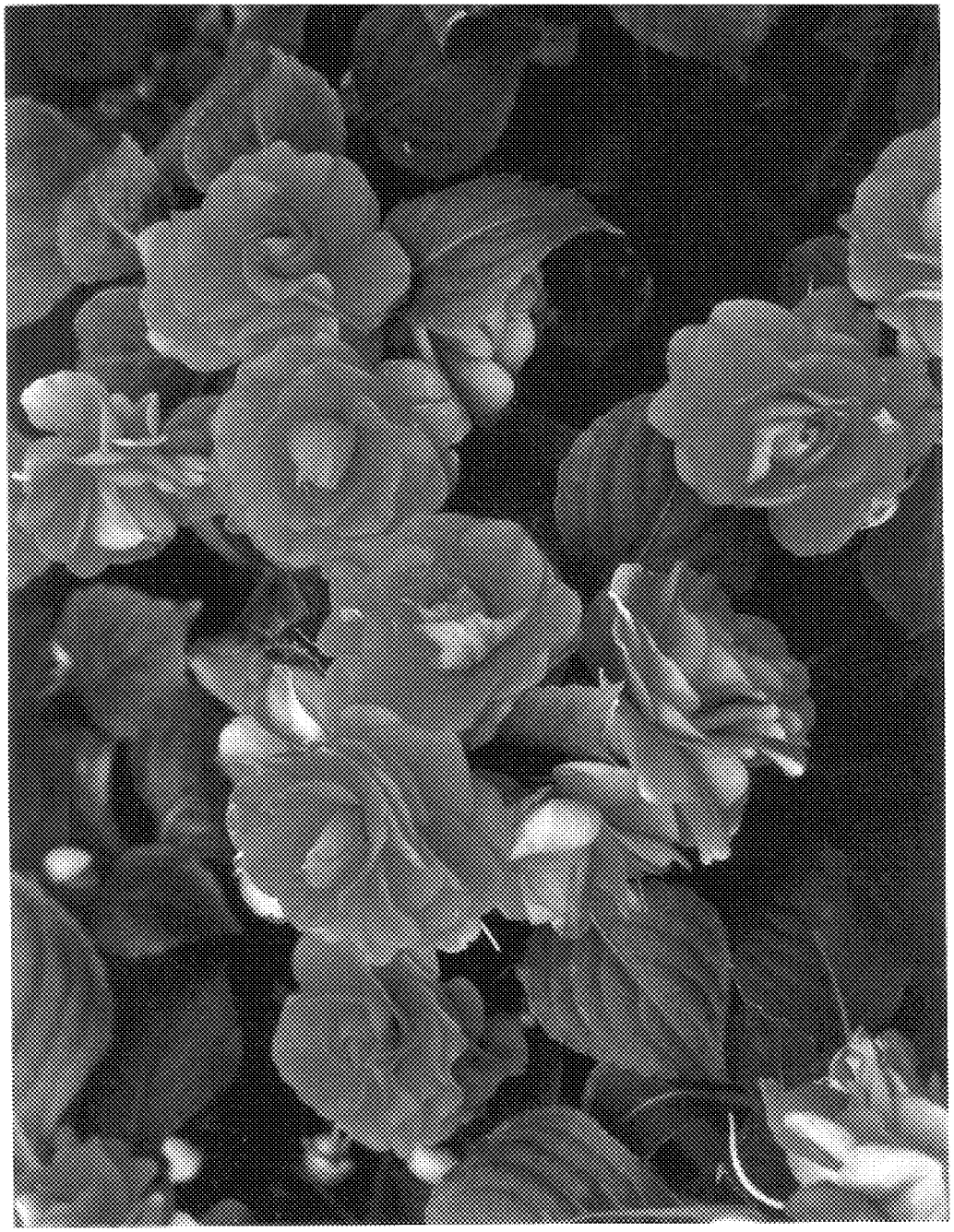

* * * * *